(12) United States Patent
Cooper

(10) Patent No.: US 6,958,766 B2
(45) Date of Patent: Oct. 25, 2005

(54) DENTAL VIDEO IMAGING SYSTEM (75) Inventor: David H. Cooper, Carlsbad, CA (US)

(73) Assignee: Gendex Corporation, Washington, DC (US)

( * ) Notice: Subject to any disclaimer, the term of this patent is extended or adjusted under 35 U.S.C. 154(b) by 767 days.

(21) Appl. No.: 09/827,997

(22) Filed: Apr. 6, 2001

(65) Prior Publication Data
US 2004/0218039 A1 Nov. 4, 2004

Related U.S. Application Data
(60) Provisional application No. 60/195,558, filed on Apr. 6, 2000.

(51) Int. Cl.$^7$ ................................................. H04N 7/18
(52) U.S. Cl. ....................................................... 348/66
(58) Field of Search ........................ 348/65–66, 72–73; 433/37, 114; 600/101, 109, 112, 122, 129, 131, 160

(56) References Cited

U.S. PATENT DOCUMENTS

| | | |
|---|---|---|
| 4,398,811 A | 8/1983 | Nishioka et al. |
| 4,475,805 A | 10/1984 | Omi |
| 4,491,865 A | 1/1985 | Danna et al. |
| 4,539,586 A | 9/1985 | Danna et al. |
| 4,572,164 A | 2/1986 | Yoshida et al. |
| 4,601,284 A | 7/1986 | Arakawa et al. |
| 4,667,229 A | 5/1987 | Cooper et al. |
| 4,677,470 A | 6/1987 | Cooper et al. |
| 4,692,608 A | 9/1987 | Cooper et al. |
| 4,727,416 A | 2/1988 | Cooper et al. |
| 4,742,388 A | 5/1988 | Cooper et al. |
| 4,757,381 A | 7/1988 | Cooper et al. |
| 4,759,347 A | 7/1988 | Ando |
| 4,858,001 A | 8/1989 | Milbank et al. |
| 4,947,245 A | 8/1990 | Ogawa et al. |
| 5,016,098 A | 5/1991 | Cooper et al. |
| 5,049,070 A | 9/1991 | Ademovic |
| 5,051,823 A | 9/1991 | Cooper et al. |
| 5,051,824 A | 9/1991 | Nishigaki |
| 5,115,307 A | 5/1992 | Cooper et al. |
| 4,858,001 A | 6/1992 | Milbank et al. |
| 5,124,797 A | 6/1992 | Williams et al. |
| 4,727,416 A | 4/1993 | Cooper et al. |
| 5,251,025 A | 10/1993 | Cooper et al. |
| 5,290,168 A | 3/1994 | Cooper et al. |
| 5,408,992 A | 4/1995 | Hamlin et al. |
| 5,429,502 A | 7/1995 | Cooper et al. |
| 5,487,661 A | 1/1996 | Peithman |
| 5,512,036 A | 4/1996 | Tamburrino et al. |
| 5,523,782 A | 6/1996 | Williams |
| 5,527,261 A | 6/1996 | Monroe et al. |

(Continued)

FOREIGN PATENT DOCUMENTS

| | | |
|---|---|---|
| JP | 9299328 | 11/1997 |
| NL | 1007059 | 12/1998 |
| WO | WO 98/02085 | 1/1998 |

*Primary Examiner*—Vu Le
(74) *Attorney, Agent, or Firm*—Brian T. Sattizahn; McNees Wallace & Nurick LLC

(57) ABSTRACT

A dental video imaging system includes a housing having a handle portion and a distal end portion. The distal end portion has a view port for viewing intra- and extra-oral dental anatomy. An optical system is mounted in the distal end of the housing for acquiring, orienting and transmitting an image of the dental anatomy appearing in said view port. A sensor assembly, mounted in the distal end of the housing, converts images received through the optical system into video data signals. A camera control unit (CCU) is mounted in the handle portion of the housing. The CCU includes a signal processor for receiving the video data image signal from the sensor and then providing a S-video, composite video or digital video signal output of the images.

70 Claims, 7 Drawing Sheets

U.S. PATENT DOCUMENTS

| | | |
|---|---|---|
| 5,527,262 A | 6/1996 | Monroe et al. |
| 5,528,432 A | 6/1996 | Donahoo |
| 5,661,519 A | 8/1997 | Franetzki |
| 5,662,586 A | 9/1997 | Monroe et al. |
| 5,675,378 A | 10/1997 | Takasugi et al. |
| 5,690,605 A | 11/1997 | Hamlin et al. |
| 5,701,155 A | 12/1997 | Wood et al. |
| 5,701,904 A | 12/1997 | Simmons et al. |
| 5,702,249 A * | 12/1997 | Cooper ............ 433/29 |
| 5,737,013 A | 4/1998 | Williams et al. |
| 5,745,165 A | 4/1998 | Atsuta et al. |
| 5,759,030 A | 6/1998 | Jung et al. |
| 5,771,067 A | 6/1998 | Williams et al. |
| 5,836,762 A | 11/1998 | Peithman |
| 5,847,759 A | 12/1998 | Williams et al. |
| 5,851,113 A | 12/1998 | Jung et al. |
| 5,871,351 A | 2/1999 | Jung et al. |
| 5,879,289 A | 3/1999 | Yarush et al. |
| 5,885,214 A | 3/1999 | Monroe et al. |
| 5,896,166 A | 4/1999 | D'Alfonso et al. |
| 5,947,729 A | 9/1999 | Bell |
| 6,002,424 A | 12/1999 | Rapa et al. |
| 6,043,839 A | 3/2000 | Adair et al. |
| 6,181,369 B1 | 1/2001 | Ooshima et al. |
| 6,190,309 B1 * | 2/2001 | Ooshima et al. ............ 600/179 |
| 6,201,880 B1 | 3/2001 | Elbaum et al. |
| 6,753,901 B1 * | 6/2004 | Takahashi et al. ............ 348/65 |

\* cited by examiner

DENTAL VIDEO IMAGING SYSTEM

CROSS-REFERENCE TO RELATED APPLICATIONS

This application claims the benefit of U.S. Provisional Patent Application No. 60/195,558 filed on Apr. 6, 2000.

BACKGROUND OF THE INVENTION

The present invention is related generally to the field of video imaging systems. Specifically, the present invention is related to a dental video imaging system that has camera control unit (CCU) circuitry for the video camera incorporated within the camera handpiece.

Video cameras for imaging dental anatomy are well known in the market place and described in the prior art. For example, Cooper in U.S. Pat. No. 5,702,249, which is incorporated herein by reference, describes DENTSPLY's Acucam® Dental Imaging Camera. These imaging cameras consist of a handpiece having a distal end that contains optics and a sensor assembly for acquiring an image of dental anatomy either intra- or extra-orally. The acquired image is typically transmitted to a docking module for a docking station or directly to an interface unit using a cable with 16 or more wires for subsequent processing before the image is displayed to the clinician. The length of the cable between the handpiece and the docking module or the interface unit is usually restricted to 2 or 3 meters before the degradation of sensor pulses starts to substantially affect the quality of the image.

Figure 7:
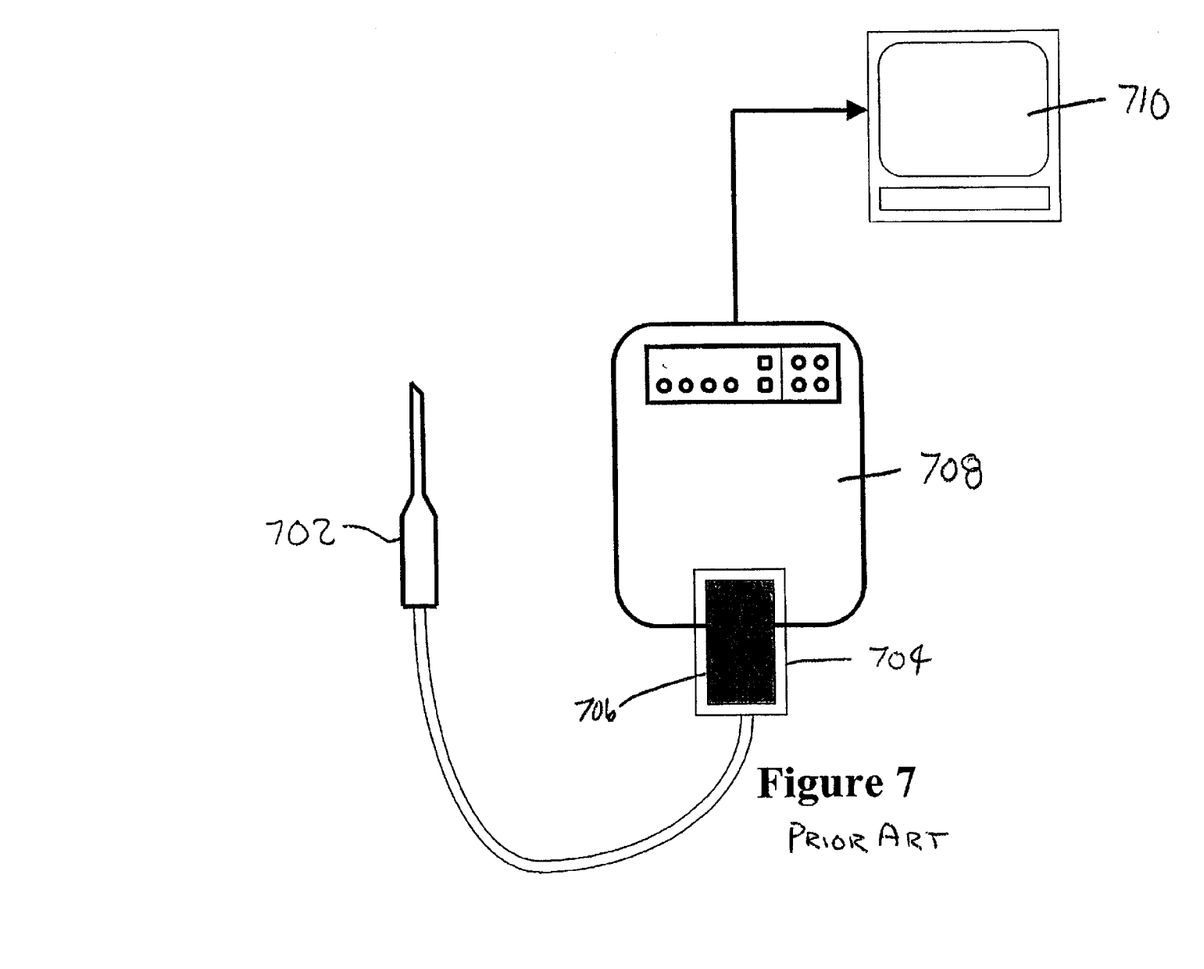
FIG. 7 is a schematic view of a prior art video imaging system.

FIG. 7 illustrates an arrangement of a docking module and docking station as used with a conventional camera. The conventional camera 702 is connected to a docking module 704 that contains a CCU 706. The docking module 704 with the CCU 706 is then plugged into a docking station 708. The docking station 708 is connected to a video monitor 710 for the clinician to view the images acquired with the conventional camera 702. Alternatively, the conventional camera 702 can be connected to an interface unit (not shown) that has a CCU 706. The interface unit would then be connected to the video monitor 710 for the clinician to view the images acquired with the conventional camera 702. Further, since much of the imaging needed is intra-oral, it is a continuing goal of the developing technology to miniaturize and make the components as small as possible.

Therefore what is needed is a dental imaging system that has a camera handpiece and associated cables that are reduced in size and can be used at larger distances from a docking station.

SUMMARY OF THE INVENTION

The present invention is directed to a video camera imaging system for intra- and extra-oral imaging of dental anatomy. The dental video imaging system includes a housing having a handle portion and a distal end portion. The distal end portion has a view port for viewing intra- and extra-oral dental anatomy. An optical system is mounted in the distal end of the housing for acquiring, orienting and transmitting an image of the dental anatomy appearing in said view port. A sensor assembly, mounted in the distal end of the housing, converts images received through the optical system into video data signals. A camera control unit (CCU) or control circuit is mounted in the handle portion of the housing. The CCU includes a digital signal processor for receiving the video data image signal from the sensor and may have additional circuitry for providing an S-video, composite video or digital video signal output of the images. The dental video imaging system also includes a utility cable having cable components for conveying utilities (power and/or light) and control signals to the housing and for conveying video output data signals out of the CCU. Flexible cables are used for flexibly interconnecting the CCU with the sensor assembly and the utility cable. A docking station is also included for connecting the utility cable with the corresponding utilities and control signals and for receiving video output data signals for display or further processing.

A key feature and advantage of the present invention is the inclusion of the CCU within the handle portion of the handpiece to provide an S-video, composite video or digital video output, which output reduces the number of cable conductors and connections necessary for connecting the handpiece to a docking station. This arrangement results in a smaller cable of, for example, two to four connector wires, rather than the sixteen or more wires as has been previously required to output image data to a docking station or interface unit from a handpiece. In addition, this arrangement also permits the use of a longer camera cable between the handpiece and the docking station, which camera cable had been previously generally restricted to 2–3 meters.

Another advantage of the present invention is that the handpiece can be connected to a docking station or interface device by a simple connector without the need for a plug-in module containing the CCU.

Still another key feature and advantage of the present invention is that the CCU in the housing is interconnected with a CCD camera or other video sensor and a utility cable by means of flexible cables, preferably flexible printed circuits, or equivalent rigid connectors in such a manner that the CCD or sensor may be translated axially for focusing the desired dental object on the CCD or sensor.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

The present invention is described in greater detail below with reference to the following drawings.

Whenever possible, the same reference numbers will be used throughout the figures to refer to the same parts.

BRIEF DESCRIPTION OF THE PREFERRED EMBODIMENT

Figures 1, 2:
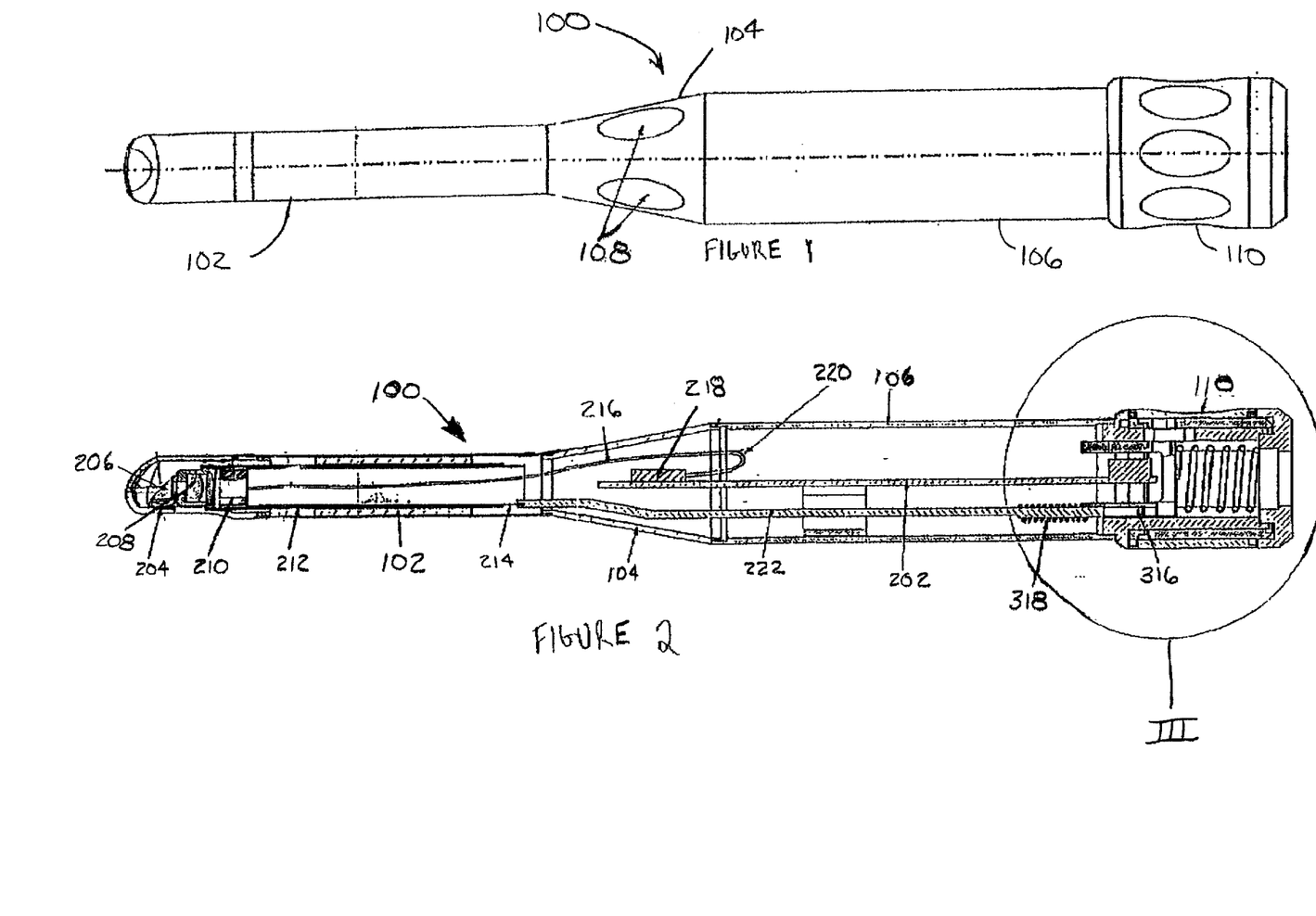
FIG. 1 is a plan view of an embodiment of the dental camera of the present invention for intra- or extra-oral imaging of desired objects of dental anatomy.
FIG. 2 is a partial section elevational view of the dental camera of FIG. 1 showing an arrangement of the CCD and CCU components of the present invention.

FIGS. 1 and 2 illustrate an embodiment of a camera head or handpiece 100 of the present invention. The camera head 100 is preferably constructed using stainless steel components, however, other suitable materials can be used. The various body components of the camera head 100 are connected together to provide a watertight casing and are preferably epoxied or glued together.

A distal end of the camera head 100 includes a nose piece 102 that is gently curved at the tip for patient comfort. The nose piece 102 is preferably stainless steel, however, any other suitable material can be used for the nose piece 102. The nose piece 102 is connected via a cone section or transitional portion 104 to a larger diameter handle region 106. The handle region 106 is configured to provide the user with an improved grasping area and a superior torque characteristic and is preferably about 20 mm in diameter.

The cone section 104 is positioned between the nose piece 102 and the handle region 106 and includes four dimples 108, which are spaced about 90° apart, to provide an orientation guide for the clinician. When normally held, the clinician's index finger is located about 45° clockwise of vertical. The dimples 108 are positioned to aid orientation of the camera head 100, as follows:

| Dimple Position | Direction of View |
| --- | --- |
| 1:30 o'clock | down |
| 4:30 o'clock | right |
| 7:30 o'clock | up |
| 10:30 o'clock | left |

A focus mode ring 110 is located at the rear of the handle region 106 and is used to select one of the following mode presets:

| Mode | Position | Depth of Focus | Application |
| --- | --- | --- | --- |
| E | Fully CCW | 40 mm to Infinity | Extra-oral use |
| W | 1st detent | 12 mm to 40 mm | Wide angle exam mode |
| C | 2nd detent | 8 mm to 12 mm | Close up exam mode |
| Macro | Continuous | 1 mm to 8 mm | Adjustable focus |

Figure 6:
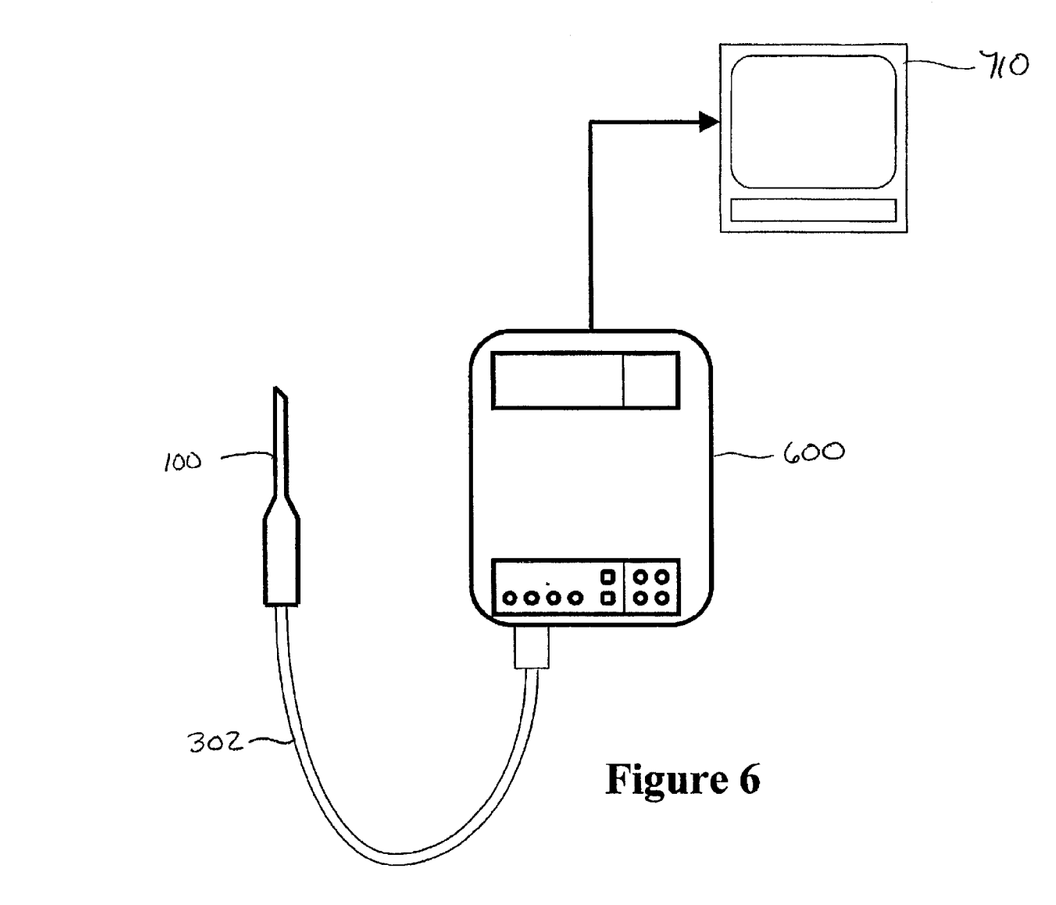
FIG. 6 is a schematic view of a video imaging system of the present invention.

FIG. 6 illustrates the camera head 100 being connected to a docking station or interface unit 600 via a small diameter connecting or utility cable 302. The docking station or interface unit 600 can then be connected to the video monitor 710 for display of the images acquired by the camera head or handpiece 100. The utility cable 302 preferably includes a spiral winding to strengthen the utility cable 302 and support any wires, fiber optic light guides, cables or conductors located therein. The spiral winding is preferably a steel spiral winding. In the embodiment shown in FIG. 3, the utility cable 302 and the wires, fiber optic light guide, cables and conductors located therein are rigidly connected to the camera handpiece 100. However, in another embodiment of the present invention, the utility cable 302 and the wires, fiber optic light guide, cables and conductors located therein are detachably connected to the camera handpiece 100.

The docking station or interface unit 600 can be any type of device that can provide the camera head 100 with the appropriate power, control and/or light for operation and can then receive the image output signals from the camera head 100 for any additional processing and display. The diameter of the connecting cable 302 is between about 0.125 and about 0.5 inches and is preferably about 0.25 inches. A smaller diameter connecting cable 302 is possible because of a control circuit or camera control unit (CCU) board 202 located in the camera head 100 as shown in FIG. 2. The CCU board 202 preferably provides an S-video output signal to a camera cable 304, located in the utility cable 302, having 4 wires for the conveying or transmitting the output signal, in contrast to the normal 16 or more wires which are usually required to convey or transmit an image output signal to a CCU located in or interface unit.

In conventional cameras, where the camera head sensor is connected to a CCU in a docking module that is plugged into a docking station or in an interface unit, the camera cable length is usually restricted to 2 or 3 meters. In contrast, in the case of the present invention, the S-video output signal from the CCU board 202 and camera cable 304 have no such restriction and the length of the connecting cable 302 is only restricted by the practical light guide limitation in fiber optic light guide 306 (see FIG. 3) also located in connecting cable 302.

The CCU board 202 is a printed circuit board with a size and shape to enable its location within the camera head 100 and handle region 106. The CCU board 202 is preferably manufactured by Matsushita Communications, Inc. (MCI). The maximum permissible width of the CCU board 202 is 17 mm for location within a handle region 106 having a 20 mm outside diameter (OD). A discussed above, a 20 mm OD for the handle region 106 is preferable for optimum user comfort and control. As shown in FIG. 2, the distal end of the CCU board 202 is tapered to fit within the conical section 104 that connects the nose piece 102 to the handle region 106. This provides additional area for the CCU board 202 without extending the length of the camera head 100.

The camera control unit board 202 includes a signal processor, which processes the signal from the image sensor 210. The signal processor is preferably a Digital Signal Processor (DSP), but can be an Analog Signal Processor. The CCU board 202 then generates the preferred S-video output signal from the CCU board 202 either from the signal processor or from additional circuitry on the CCU board 202. Additionally, in other embodiments the CCU board 202 can generate a component video or digital video output signal. It is to be understood that the wires in the camera cable 304 to transmit or convey the output signal correspond to the particular type of output signal from the CCU board 202. The signal processor is configured and adjusted by digital commands from a computer via 3 wires in the camera cable 304. This enables the CCU board 202 to be adjusted after the camera head 100 has been assembled and closed. Non-volatile memory on the CCU board 202 can be used to store the adjustments, thereby making the adjustments permanent.

Figure 3:
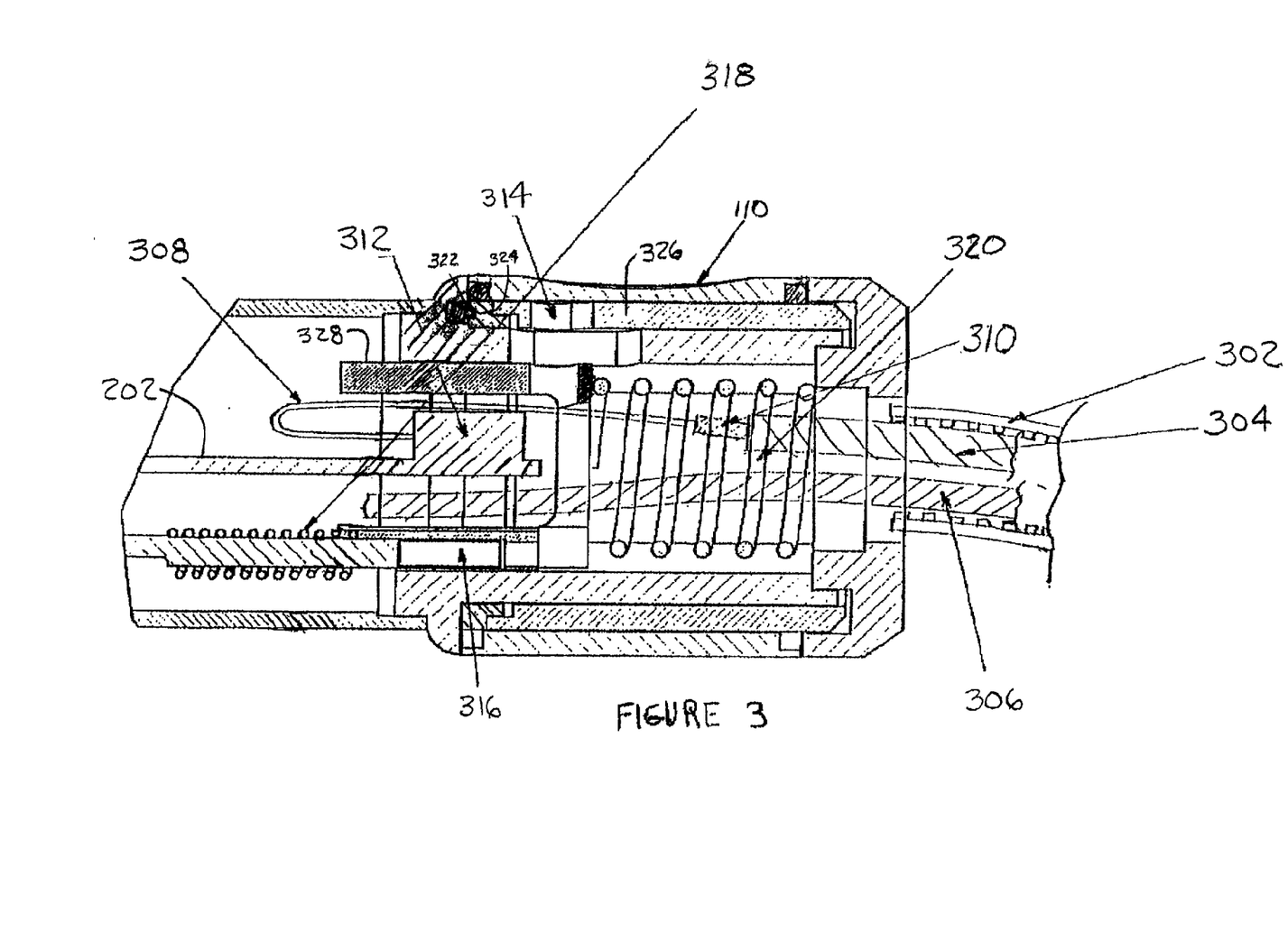
FIG. 3 is an enlarged elevational cross sectional view of the focusing arrangement of FIG. 2.

As described above, the connecting or utility cable 302 includes the camera cable 304, which is preferably shielded, and the fiber optic light guide 306. The camera cable 304 is connected to a flexible printed circuit 308 by an encapsulated connection 310 in the camera head 100. The flexible printed circuit 308 is then connected to the CCU board 202 by a connector 312. The camera cable 304 includes wires or conductors to convey or transmit the following signals and information:

power to the CCU board 202;

computer control data to the CCU board 202; and video output signals from the CCU board 202.

Referring back to FIG. 2, an image enters an optical system through a window 204 into a negative lens and a non-inverting prism 206. The window 204 is preferably sapphire, but can also be glass or acrylic. The non-inverting prism 206 is preferably a roof prism or double prism and reflects the image into a main lens assembly 208. The roof prism 206 is angled to obtain a 97.5° direction of view with respect to the optical axis. The negative lens enables a relatively wide angle of view of 62° horizontally through the window 204 by converting the wide angle to a narrow angle for the roof prism 206. This enables a wider viewing angle than can otherwise pass through the prism. It is to be understood that different directions of view and angles of view can be obtained by selecting the appropriate roof prism 206 and/or negative lens.

In another embodiment of the present invention, a simple inverting prism can be used in place of the non-inverting roof prism 206. In this embodiment, an inverted image is sent to the CCU board 202, which includes the appropriate circuitry to orient the image. In still another embodiment of the present invention, the use of the negative lens is not required, and a wide angle image can be sent by the optical system to the CCU board 202.

The main lens assembly 208 is housed in a barrel or enclosure that is connected to a thin-wall lens tube 212, preferably by gluing with epoxy. The lens tube 212 is held in place within the nose piece 102 by a lens holder spacer. The lens tube 212 is preferably stainless steel, although other suitable materials can be used. The preferred embodiment of the main lens assembly 208 includes three elements: a plano-convex lens; a doublet; and a simple lens. The simple lens focuses the image onto an image sensor 210. The image sensor 210 is preferably a ¼-inch, high resolution CCD. However, other types of images sensors can be used such as CMOS devices and active pixel sensors (APS).

To supply light to the camera head 100, one end of the fiber optic light guide 306 terminates in a metal ferrule at the center of a modified Lemo connector (not shown), which passes through the docking station receptacle and enters a port in a light source.

In the connecting cable 302, the light guide 306 is covered by a thin plastic sheath, which continues into the handle portion or region 106 of the camera head 100. In the handle region 106, the light guide 306 separates or bifurcates into two equal bundles (not shown), which pass through the nose piece 102 on either side of the lens tube 212 that holds the main lens assembly 208 via curved slots in the lens holder spacer and terminate on either side of the window 204. By splitting the light guide 306 into two bundles, a more uniform illumination for the optical system can be provided than with a single light guide.

At the tip of the distal end, the light guide bundles are covered in a thin-wall opaque sheath or paint, to prevent light from entering the optical system, and terminate in a ferrule that is glued into the exit ports of the distal end. The ferrules are shaped in such a way as to ensure that the angle of illumination corresponds to the direction of view of the optical system.

In another embodiment of the present invention, a thin-wall opaque barrier is placed between the optical system and the light guides to block stray light and prevent light from the light guide bundles from entering the optical system. The opaque barrier is preferably a metal material, however, the barrier can be made of any suitable material such as plastic, paper or other material.

The image sensor 210 is supported in a sensor tube 214, which is preferably stainless steel. The sensor tube 214 is permitted to slide within the lens tube 212 that holds the optical system and main lens assembly 208. The image sensor 210 is connected by a flexible printed circuit 216 to a connector 218 on the CCU board 202 located in the camera head 100, as shown in FIG. 2.

In order to adjust the focus mode, the position of the sensor tube 214 and the image sensor 210 relative to the main lens assembly 208 is adjusted by movement of a focus rod 222 connected to the sensor tube 214. The adjustment of the focus mode is accomplished by rotating the focus mode ring 110 at the rear of the handle region 106, as detailed in FIG. 3. Furthermore, the flexible printed circuit 216 has a service loop 220 over the CCU connector 218, so that the loop length for the flexible circuit 216 can adjust when the image sensor 210 and sensor tube 214 are moved by the focus rod 222.

A focus mode assembly includes the focus mode ring 110, which is connected, preferably by gluing, to an inner focus ring 322 with an angled slot 314. When the focus mode ring 110 is adjusted, the inner focus ring 322 with the angled slot 314 causes a pin 504 (see FIG. 5) inserted into angled slot 314 to move in the direction of the camera axis. The pin 504 is attached to a linear ring 328 that is connected to one end of the focus rod 222, which focus rod 222 is then connected to the sensor tube 214 at the other end. Therefore, movement of the focus mode ring 110 results in the sensor tube 214 and the sensor 210 to moving axially, thereby changing the sensor's position relative to the main lens assembly 208 and thereby changing the sensor's focal condition.

Due to tolerances in the lenses of the optical system, the positioning of the sensor 210 relative to the optical system has to be adjusted to obtain an optimal focal length for the focus modes. A focus calibration screw 316 and calibration spring 318 are used to adjust the length of the focus rod 222, so that the position of the sensor 210 relative to the optical system can compensate for the lens tolerances. The calibration spring 318 is positioned around the focus rod 222 and is used to prevent any backlash of the focus rod 222 during the adjustment of the focus rod 222 by the focus calibration screw 316. The calibration of the focus rod 222 to compensate for lens tolerance with the focus calibration screw 316 is typically completed during the manufacturing of the camera head 100. In addition, a focus spring 320 is used to apply a tension to the linear ring 328 and pin 504 to maintain the pin 504 in contact with a side of the angled slot 314 and is used to prevent any backlash of the focus mode assembly or the linear ring.

A spring-loaded ball 322 drops into a detent 324 in the focus mode assembly, providing tactile preset focus positions for each of the E, W and C modes discussed above. This enables the clinician to select the desired mode by feel, without the need to take his eyes off the patient. Each mode has sufficient depth of focus so that further fine adjustment within the mode is not necessary.

Figure 5:
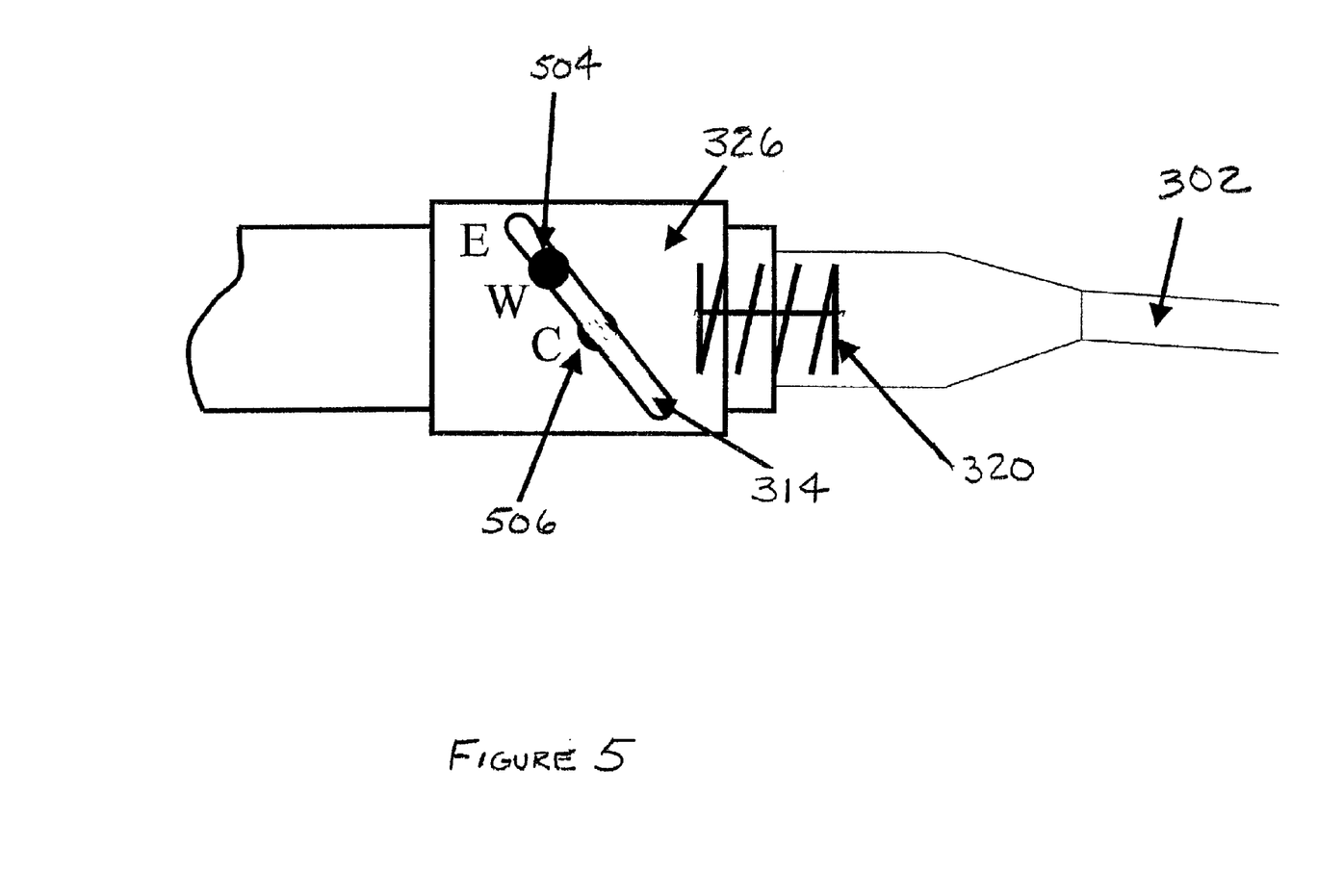
FIG. 5 is a schematic partial sectional view of an alternate embodiment of the focusing arrangement of FIG. 3.

In another embodiment of the present invention, as shown schematically in FIG. 5, a spiral slot 314 in the side of the inner focus ring 326 interacts with the focus pin 504 and linear ring 328, which linear ring 328 is then connected to the focus rod 222. The focus rod 222, as described above, is connected to the sensor tube 214 to move the sensor tube 214 longitudinally or axially as the focus mode ring 110 is rotated. Instead of the spring-loaded ball 322 and detent 324 technique shown in FIG. 3 to select the focus modes, notches 506 in the spiral slot 314 corresponding to the W and C focus mode positions are pushed against by a spring loaded linear ring 328 and pin 504. The spring loading is provided by the focus spring 320 and serves two functions: it prevents backlash in the focus adjustment; and it provides a detent action caused by the focus pin 504 being forced to engage the notches 506 as the inner focus ring 326 is rotated. In addition, the E focus mode position is established or located at one end of the spiral slot 502.

In another embodiment of the present invention, the focus rod 222 can move one or more elements of the optical system relative to the image sensor 210 to obtain the different focus modes. The focus rod 222 can be connected to one or more elements of the optical system such as the negative lens or an element in the main lens assembly 208. The adjustment of the focus rod 222 for the different focus modes is accomplished in a manner similar to that described above. The adjustment of the one or more elements in the optical system is performed relative to the sensor 210 to obtain the different focus modes, in contrast to the technique for obtaining the different focus modes described above wherein the sensor 210 is moved relative to the optical system.

Figure 4:
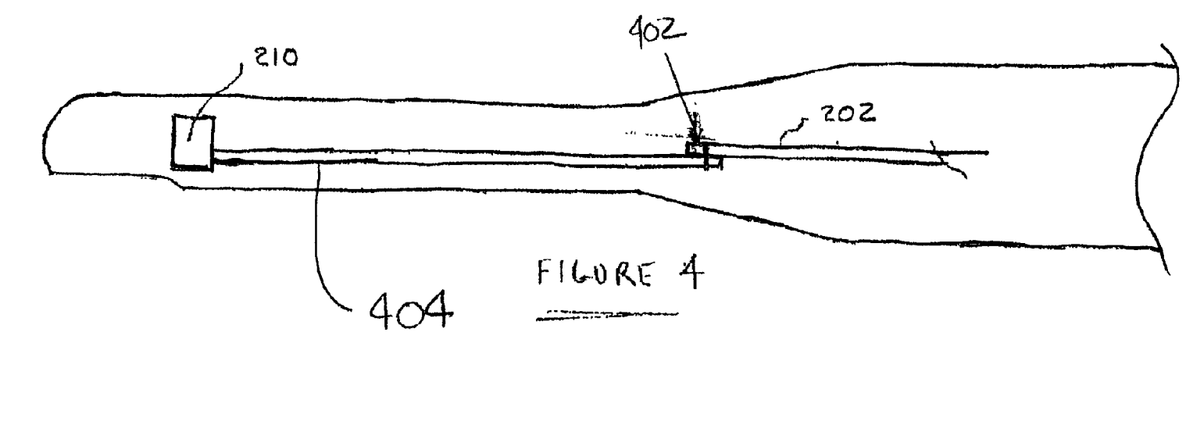
FIG. 4 is a partial sectional elevational view of a second embodiment of a focusing arrangement of the present invention.

FIG. 4 shows a second embodiment of the present invention where the image sensor 210 is connected to an extension board 404, which is rigidly connected to the CCU board 202 by a connecting arrangement 402. The connecting arrangement 402 can include any type of connection that permits axial translation of the image sensor 210 and extension board 404 without detaching from the CCU board 202. The rigidly connected image sensor 210, extension board 404 and CCU board 202 move in tandem with the CCU board 202 being connected to the camera cable 304 as previously described. The adjustment of the focus modes occurs based on the axial movement of the CCU board 202 and image sensor 210 in response to the adjustment of the focus mode ring 110 as described above except that no focus rod 222 is used and the linear ring 328 is connected to the CCU board 202. Movement of the CCU board 202 relative to the utility cable 302 is provided by the service loop in the flexible cable 308 as shown in FIG. 3. In another embodiment of the present invention, the extension board 404 can be an included and integral part of the CCU board 202.

Figure 8:
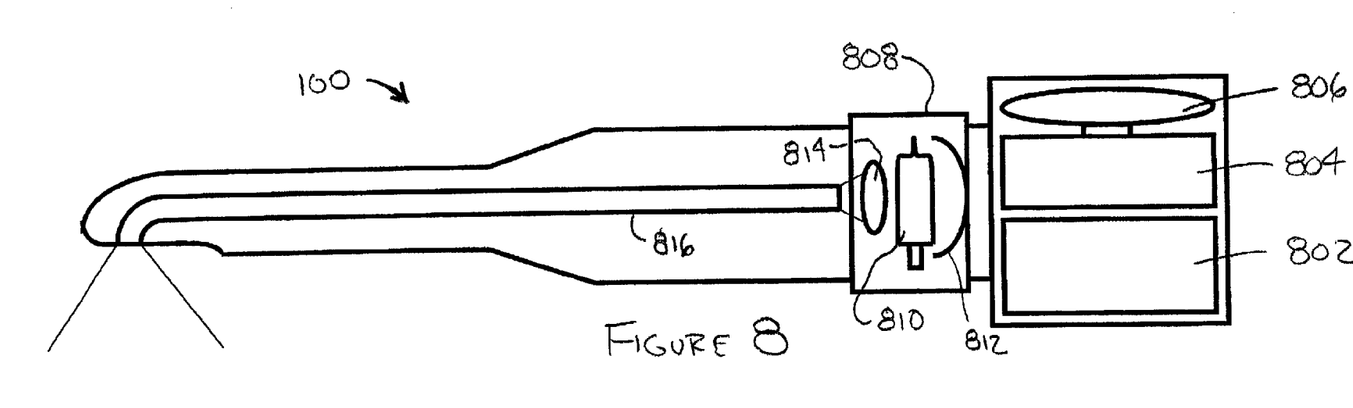
FIGS. 8 and 9 are alternate embodiments of the dental camera of the present invention.

FIG. 8 illustrates an alternate embodiment of the present invention, where the utility cable 302 has been replaced by a utility and communication unit. The utility and communication unit can include several different systems to satisfy all of the utility and communication requirements of the camera handpiece 100. The utility and communication unit can be detachably connected to the camera handpiece 100. The utility and communication unit can include a battery 802 to supply the power requirements of the CCU board 202 and other systems and devices in the camera handpiece 100 and the utility and communication unit. The utility and communication unit also includes a transmitter unit 804 and antenna 806 to transmit the video output signal from the CCU board 202. The transmitter unit 804, in one embodiment, may include a receiver to receive transmissions with control instructions and other information for the CCU board 202. The transmitter unit 804 and the antenna 806 can receive their power from the battery 802. The transmitter unit 804 can transmit the video output signals using any standard wireless transmission technique, including infrared and RF transmissions, to a receiver that is preferably connected to a computer, monitor, docking station, interface unit, etc. The utility and communication unit has a light or illumination source 808 to satisfy the lighting requirements of the camera head 100. The light source 808 includes a lamp 810, a reflector 812, and a lens 814. The lens 814 transmits the light to a light guide 816, which is used to transmit the light to the tip of the nose piece 102. The battery 802 can preferably be used to supply the required power to the light source 808.

Figure 9:
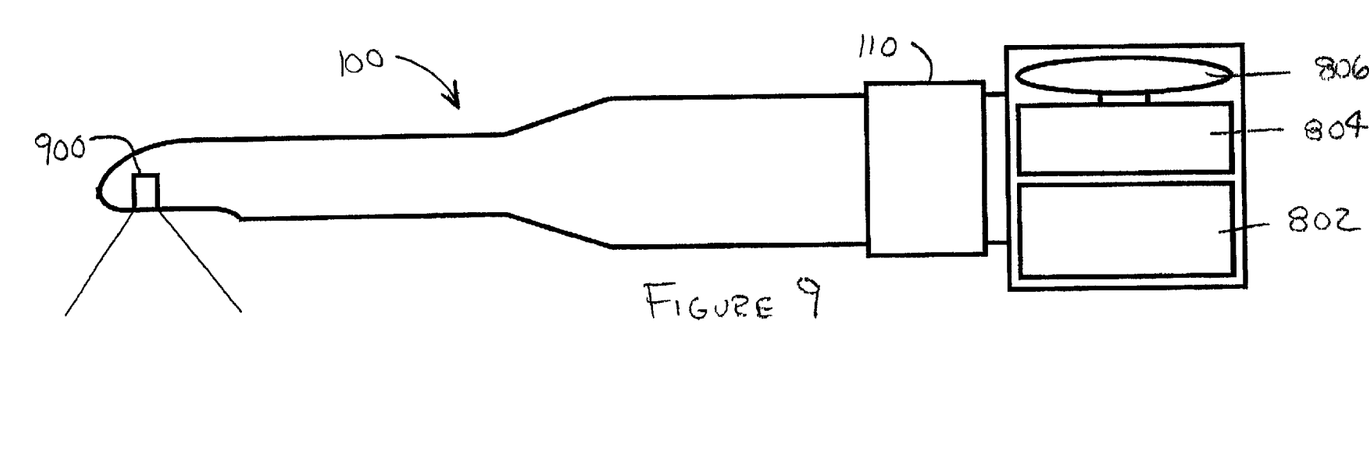

FIG. 9 illustrates another embodiment of the camera handpiece 100 wherein the light source 808 is replaced with one or more light emitting diodes (LEDs) 900 located in the tip of the nose piece 102. The LEDs 900 can be white LEDs or a combination of colored LEDs and can be placed in the exit ports at the distal end and have the same opaque barrier or sheaths to prevent light from entering the optical system as described above. Alternatively, the LEDs 900 can be located elsewhere in the camera handpiece 100, e.g. in the handle region 106, and the light transmitted to the distal end of the camera handpiece 100 by a light guide.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dental imaging system, comprising:
    a handpiece including a handle portion and a distal end portion, said distal end portion having a view port for viewing intra- and extra-oral dental anatomy;
    an optical system mounted in said distal end portion of said handpiece, said optical system being configured to acquire, orient and transmit an image of said dental anatomy appearing in said view port;
    a sensor assembly mounted in said distal end of said handpiece, said sensor assembly being configured to convert images received through said optical system into video data signals;
    a camera control unit mounted in said handle portion of said handpiece, said camera control unit being configured to receive said video data signals from said sensor assembly and to generate video output signals of said image from said video data signals;
    a connector disposed in said handpiece to flexibly interconnect said camera control unit with said sensor assembly, wherein said connector is configured to permit axial adjustment of said sensor assembly for focusing on said dental anatomy; and
    an interface means connected to said camera control unit for providing power to said camera control unit and for receiving video output signals from said camera control unit for transmission to a device for display or further processing.

2. The dental imaging system of claim 1 where said interface means comprises a utility cable, said utility cable connecting said handpiece to one of an interface unit or a docking station, said utility cable comprises a camera cable having first cable components to convey said power to said camera control unit from said one of an interface unit or a docking station and second cable components to convey said video output signals from said camera control unit to said one of an interface unit or a docking station.

3. The dental imaging system of claim 2 wherein said second cable components comprise conductors to convey one of S-video signals, composite video signals or digital video signals.

4. The dental imaging system of claim 3 wherein said second cable components comprise conductors to convey S-video signals.

5. The dental imaging system of claim 2 wherein said utility cable further comprises a fiber optic light guide to transmit light from said one of an interface unit or a docking station to said handpiece.

6. The dental imaging system of claim 2 wherein said camera cable comprises third cable components to convey control signals to said camera control unit from said one of an interface unit or a docking station.

7. The dental imaging system of claim 2 wherein said optical system comprises:
   a window to acquire said image of said dental anatomy;
   a prism to reflect said image of said dental anatomy acquired from said window; and
   a lens assembly to transmit said image of said dental anatomy received from said prism to said sensor assembly.

8. The dental imaging system of claim 7 wherein said optical system further comprises a negative lens.

9. The dental imaging system of claim 7 wherein said prism is a non-inverting prism.

10. The dental imaging system of claim 1 wherein said interface means comprises a battery to supply power to said camera control unit.

11. The dental imaging system of claim 1 wherein said interface means comprises a wireless transmission system to transmit said video output signals from said camera control unit to a remote receiver.

12. The dental imaging system of claim 1 wherein said interface means are detachably connected to said handpiece.

13. The dental imaging system of claim 1 further comprises an illumination source.

14. The dental imaging system of claim 13 wherein said illumination source comprises a lamp, a reflector and a lens.

15. The dental imaging system of claim 14 wherein said handpiece further comprises a light guide to receive light from said lens and transmit said light to said distal end portion of said handpiece.

16. The dental imaging system of claim 13 wherein said illumination source comprises at least one light emitting diode.

17. The dental imaging system of claim 1 further comprising one of an interface unit or a docking station to receive said video output signals from said camera control unit.

18. The dental imaging system of claim 1 further comprising:
   a connector to flexibly interconnect said interface means and said camera control unit circuit.

19. The dental imaging system of claim 18 wherein:
   said connector to flexibly interconnect said camera control unit with said sensor assembly comprises a flexible printed circuit; and
   said connector to flexibly interconnect said interface means and said camera control unit comprises a flexible printed circuit.

20. The dental imaging system of claim 19 wherein said flexible printed circuit to interconnect said camera control unit with said sensor assembly is positioned in an elongated loop to permit axial adjustment of said sensor assembly for focusing on said dental anatomy.

21. The dental imaging system of claim 18 wherein said connector to flexibly interconnect said camera control unit with said sensor assembly comprises an extension board rigidly connected to said camera control unit and said sensor assembly such that said camera control unit and said sensor assembly are axially adjustable in tandem for focusing said sensor assembly upon said dental anatomy.

22. The dental imaging system of claim 1 wherein said video output signals from said camera control unit comprise one of S-video signals, composite video signals or digital video signals.

23. The dental imaging system of claim 1 wherein said camera control unit comprises one of a digital signal processor or an analog signal processor.

24. The dental imaging system of claim 1 wherein said sensor assembly comprises one of a charge coupled device, a CMOS device or an active pixel sensor.

25. The dental imaging system of claim 1 wherein said sensor assembly is axially adjustable into a plurality of predetermined focus modes to focus on said dental anatomy.

26. The dental imaging system of claim 25 wherein each of said plurality of predetermined focus modes is selected by adjusting a ring in said handle region of said handpiece, said ring being operatively connected to an assembly for axial adjusting said sensor assembly such that an adjustment in said ring results in said assembly axially adjusting said sensor assembly to correspond to a predetermined focus mode.

27. The dental imaging system of claim 1 wherein a plurality of predetermined focus modes are selected by adjusting a ring in said handle region of said handpiece, said ring being operatively connected to an assembly for axial adjusting at least one element of said optical system relative to said sensor assembly such that an adjustment in said ring results in said assembly axially adjusting said at least one element of said optical system to correspond to a predetermined focus mode.

28. The dental imaging system of claim 1 wherein said handpiece comprises a conical section between said handle portion and said distal end portion, said conical section having plurality of orientation dimples spaced circumferentially about said conical section, wherein holding said conical section of said housing with an index finger positioned in an orientation dimple orients said view port in a preselected viewing direction.

29. A camera handpiece for a dental imaging system, said camera handpiece comprising:
   a housing including a handle portion and a distal end portion, said distal end portion having a view port for viewing intra- and extra-oral dental anatomy;
   an optical system mounted in said distal end portion of said housing, said optical system being configured to acquire and transmit an image of said dental anatomy appearing in said view port;
   a sensor assembly mounted in said distal end of said housing, said sensor assembly being configured to convert images received through said optical system into video data signals;
   a camera control unit mounted in said handle portion of said housing, said camera control unit being configured to receive said video data signals from said sensor assembly and to generate video output signals of said image from said received video data signals;
   a connector disposed in said housing to flexibly interconnect said camera control unit with said sensor assembly, wherein said connector is configured to permit axial adjustment of said sensor assembly for focusing on said dental anatomy; and
   an interface means connected to said camera control unit for providing power to said camera control unit and for receiving video output signals from said camera control unit for transmission to a device for display or further processing.

30. The camera handpiece of claim 29 wherein said interface means further comprises means for conveying control signals to said camera control unit.

31. The camera handpiece of claim 30 wherein the interface means comprises a cable interface to connect a utility cable to said camera handpiece.

32. The camera handpiece of claim 31 wherein said cable interface is configured to provide a detachable connection between said utility cable and said camera handpiece.

33. The camera handpiece of claim 29 wherein said interface means comprises a battery to supply power to said camera control unit.

34. The camera handpiece of claim 29 wherein said interface means comprises a wireless transmission system to transmit said video output signals from said camera control unit to a remote receiver.

35. The camera handpiece of claim 34 wherein said wireless transmission system composes a transmitter and an antenna.

36. The camera handpiece of claim 29 further comprises an illumination source.

37. The camera handpiece of claim 36 wherein said illumination source comprises a lamp, a reflector and a lens.

38. The camera handpiece of claim 37 further comprises a light guide to receive light from said lens and transmit said light to said distal end portion of said handpiece.

39. The camera handpiece of claim 36 wherein said illumination source comprises at least one light emitting diode.

40. The camera handpiece of claim 29 further comprising:
a connector to flexibly interconnect said interface means and said camera control unit.

41. The camera handpiece of claim 40 wherein:
said connector to flexibly interconnect said camera control unit with said sensor assembly comprises a flexible printed circuit; and
said connector to flexibly interconnect said interface means and said camera control unit comprises a flexible printed circuit.

42. The camera handpiece of claim 41 wherein said flexible printed circuit to interconnect said camera control unit with said sensor assembly is positioned in an elongated loop to permit axial adjustment of said sensor assembly for focusing on said dental anatomy.

43. The camera handpiece of claim 40 wherein said connector to flexibly interconnect said camera control unit with said sensor assembly comprises a rigid connection between said camera control unit and said sensor assembly such that said camera control unit and said sensor assembly are axially adjustable in tandem for focusing said sensor assembly upon said dental anatomy.

44. The camera handpiece of claim 29 wherein said video output signals from said camera control unit comprise one of S-video signals, composite video signals or digital video signals.

45. The camera handpiece of claim 29 wherein said sensor assembly comprises one of a charge coupled device, a CMOS device or an active pixel sensor.

46. The camera handpiece of claim 29 wherein said camera control unit comprises one of a digital signal processor or an analog signal processor.

47. The camera handpiece of claim 29 wherein said sensor assembly is axially adjustable into a plurality of predetermined focus modes to focus on said dental anatomy.

48. The camera handpiece of claim 47 wherein each of said plurality of predetermined focus modes is selected by adjusting a ring in said handle region of said housing, said ring being operatively connected to an assembly for axial adjusting said sensor assembly such that an adjustment in said ring results in said assembly axially adjusting said sensor assembly to correspond to a predetermined focus mode.

49. The camera handpiece of claim 29 wherein said housing comprises a conical section between said handle portion and said distal end portion, said conical section having plurality of orientation dimples spaced circumferentially about said conical section, wherein holding said conical section of said housing with an index finger positioned in an orientation dimple orients said view port in a preselected viewing direction.

50. The camera handpiece of claim 29 wherein said optical system comprises:
a window to acquire said image of said dental anatomy;
a prism to reflect said image of said dental anatomy acquired from said window; and
a lens assembly to transmit said image of said dental anatomy received from said prism to said sensor assembly.

51. The camera handpiece of claim 50 wherein said optical system further comprises a negative lens.

52. The camera handpiece of claim 50 wherein said prism is a non-inverting prism.

53. The camera handpiece of claim 50 wherein:
said prism is an inverting prism; and
said camera control unit comprises orienting circuitry to orient said image received from said sensor assembly.

54. The camera handpiece of claim 29 wherein said camera control unit comprises a non-volatile memory to store control instructions for said camera control unit.

55. The camera handpiece of claim 29 wherein a plurality of predetermined focus modes are selected by adjusting a ring in said handle region of said housing, said ring being operatively connected to an assembly for axial adjusting at least one element of said optical system relative to said sensor assembly such that an adjustment in said ring results in said assembly axially adjusting said at least one element of said optical system to correspond to a predetermined focus mode.

56. A dental imaging system, comprising:
a handpiece including a handle portion and a distal end portion, said distal end portion having a view port for viewing intra- and extra-oral dental anatomy;
an optical system mounted in said distal end portion of said handpiece, said optical system being configured to acquire, orient and transmit an image of said dental anatomy appearing in said view port;
a sensor assembly mounted in said distal end of said handpiece, said sensor assembly being configured to convert images received through said optical system into video data signals;
a camera control unit mounted in said handle portion of said handpiece, said camera control unit being configured to receive said video data signals from said sensor assembly and to generate video output signals of said image from said video data signals;
a connector disposed in said handpiece to flexibly interconnect said camera control unit with said sensor assembly, wherein said connector is configured to permit axial adjustment of said sensor assembly for focusing on said dental anatomy; and a docking station connected to said camera control unit, said docking station being configured to provide power and control signals to said camera control unit and to receive video output signals from said camera control unit for display or further processing.

57. The dental imaging system of claim 56 further comprising a utility cable to connect said handpiece and said docking station, said utility cable comprises a camera cable having first cable components to convey said power and control signals to said camera control unit from said docking station and second cable components to convey said video output signals from said camera control unit to said docking station, and said utility cable further comprising a fiber optic light guide to transmit light from said interface unit to said handpiece.

58. The dental imaging system of claim 57 further comprising:
   said connector comprising a flexible printed circuit; and
   a flexible printed circuit to flexibly interconnect said camera cable and said camera control unit circuit.

59. The dental imaging system of claim 56 wherein said sensor assembly is a charge coupled device.

60. The dental imaging system of claim 56 wherein said sensor assembly is axially adjustable into a plurality of predetermined focus modes to focus on said dental anatomy and each of said plurality of predetermined focus modes is selected by adjusting a ring in said handle region in said handpiece.

61. The dental imaging system of claim 56 wherein said handpiece comprises a conical section between said handle portion and said distal end portion, said conical section having plurality of orientation dimples spaced circumferentially about said conical section, wherein holding said conical section of said handpiece with an index finger positioned in an orientation dimple orients said view port in a preselected viewing direction.

62. The dental imaging system of claim 56 wherein said camera control unit comprises a digital signal processor and means for generating a video output signal in an S-video format.

63. The dental imaging system of claim 56 wherein said optical system comprises:
   a window to acquire said image of said dental anatomy;
   a negative lens to pass a narrow angle image of said acquired image;
   a non-inverting prism to reflect said narrow angle image of said dental anatomy passed by said negative lens; and
   a lens assembly to transmit said narrow angle image of said dental anatomy received from said prism to said sensor assembly.

64. A camera handpiece for a dental imaging system, said camera handpiece comprising:
   a housing including a handle portion and a distal end portion, said distal end portion having a view port for viewing intra- and extra-oral dental anatomy;
   an optical system mounted in said distal end portion of said housing, said optical system being configured to acquire and transmit an image of said dental anatomy appearing in said view port;
   a sensor assembly mounted in said distal end of said housing, said sensor assembly being configured to convert images received through said optical system into video data signals;
   a camera control unit mounted in said handle portion of said housing, said camera control unit being configured to receive said video data signals from said sensor assembly and to generate video output signals of said image from said received video data signals;
   a cable interface to connect a utility cable to said camera handpiece; and
   a connector to flexibly interconnect said camera control unit with said sensor assembly, wherein said connector is configured to permit axial adjustment of said sensor assembly for focusing on said dental anatomy.

65. The camera handpiece of claim 64 further comprising:
   said connector comprising a flexible printed circuit; and
   a flexible printed circuit to flexibly interconnect said cable interface and said camera control unit.

66. The camera handpiece of claim 64 wherein said sensor assembly is a charge coupled device.

67. The camera handpiece of claim 64 wherein said sensor assembly is axially adjustable into a plurality of predetermined focus modes to focus on said dental anatomy and each of said plurality of predetermined focus modes is selected by adjusting a ring in said handle region in said handpiece.

68. The camera handpiece of claim 64 wherein said handpiece comprises a conical section between said handle portion and said distal end portion, said conical section having plurality of orientation dimples spaced circumferentially about said conical section, wherein holding said conical section of said handpiece with an index finger positioned in an orientation dimple orients said view port in a preselected viewing direction.

69. The camera handpiece of claim 64 wherein said camera control unit comprises a digital signal processor and means for generating a video output signal in an S-video format.

70. The camera handpiece of claim 64 wherein said optical system comprises:
   a window to acquire said image of said dental anatomy;
   a negative lens to pass a narrow angle image of said acquired image;
   a non-inverting prism to reflect said narrow angle image of said dental anatomy passed by said negative lens; and
   a lens assembly to transmit said narrow angle image of said dental anatomy received from said prism to said sensor assembly.

* * * * *

UNITED STATES PATENT AND TRADEMARK OFFICE
CERTIFICATE OF CORRECTION

PATENT NO.        : 6,958,766 B2
APPLICATION NO. : 09/827997
DATED             : October 25, 2005
INVENTOR(S)       : David H. Cooper It is certified that error appears in the above-identified patent and that said Letters Patent is hereby corrected as shown below:

In column 11, line 21, "composes" should be -- comprises --

Signed and Sealed this

Twenty-seventh Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 6,958,766 B2  Page 1 of 1
APPLICATION NO. : 09/827997
DATED : October 25, 2005
INVENTOR(S) : David H. Cooper It is certified that error appears in the above-identified patent and that said Letters Patent is hereby corrected as shown below:

On the Title page, Item 56, References Cited, please add the following U.S. Patent Document
-- 6,132,211 A, 10-2000, Peithman, Keith C. --, Signed and Sealed this Eighth Day of May, 2007

JON W. DUDAS
*Director of the United States Patent and Trademark Office*